US009999560B2

(12) United States Patent
Farese et al.

(10) Patent No.: US 9,999,560 B2
(45) Date of Patent: *Jun. 19, 2018

(54) DEVICE FOR DIALYSIS AND STIMULATION OF A PATIENT AND METHOD

(71) Applicants: DJO, LLC, Vista, CA (US); Universität Bern, Bern (CH)

(72) Inventors: Stefan Farese, Solothurn (CH); Dominik Uehlinger, Kerzers (CH); Klaus Schonenberger, Vufflens-La-Ville (CH); Felix Buhlmann, Lausanne (CH)

(73) Assignees: DJO, LLC, Vista, CA (US); UNIVERSITÄT BERN, Bern (CH)

( * ) Notice: Subject to any disclaimer, the term of this patent is extended or adjusted under 35 U.S.C. 154(b) by 0 days. days.

This patent is subject to a terminal disclaimer.

(21) Appl. No.: 13/961,478

(22) Filed: Aug. 7, 2013

(65) Prior Publication Data
US 2013/0324896 A1 Dec. 5, 2013

Related U.S. Application Data

(63) Continuation of application No. 12/674,599, filed as application No. PCT/IB2008/053375 on Aug. 22, 2008, now Pat. No. 8,965,517.

(30) Foreign Application Priority Data

Aug. 22, 2007 (EP) ..................................... 07114801
Nov. 2, 2007 (EP) ..................................... 07119934

(51) Int. Cl.
A61M 1/14 (2006.01)
A61H 9/00 (2006.01)
(Continued)

(52) U.S. Cl.
CPC ........... *A61H 1/008* (2013.01); *A61H 9/0078* (2013.01); *A61M 1/16* (2013.01); *A61N 1/36003* (2013.01);
(Continued)

(58) Field of Classification Search
CPC .............................................. A61M 1/14–1/34
(Continued)

(56) References Cited

U.S. PATENT DOCUMENTS 3,699,960 A * 10/1972 Freedman ............... A61M 1/16
128/DIG. 3
4,353,368 A * 10/1982 Slovak ................ A61M 1/1656
210/646

(Continued)

FOREIGN PATENT DOCUMENTS

EP 0211146 A1 2/1987
WO WO-03024371 A1 3/2003
(Continued)

OTHER PUBLICATIONS

Trisha L. Parsons, Edwin B. Toffelmire, Cheryl E. King-VanVlack, Exercise Training During Hemodialysis Improves Dialysis Efficacy and Physical Performance, Archives of Physical Medicine and Rehabilitation, vol. 87, Issue 5, May 2006, pp. 680-687, ISSN 0003-9993, http://dx.doi.org/10.1016/j.apmr.2005.12.044.*

(Continued)

*Primary Examiner* — Eugene T Wu
*Assistant Examiner* — Eugene Wu
(74) *Attorney, Agent, or Firm* — Knobbe Martens Olson & Bear LLP

(57) ABSTRACT

A device and method for carrying out dialysis and stimulation of a patient at the same time, in which an inflatable/deflatable cuff applies the stimulation.

23 Claims, 2 Drawing Sheets

(51) Int. Cl.
*A61H 1/00* (2006.01)
*A61N 1/36* (2006.01)
*A61M 1/16* (2006.01)
*A61N 1/04* (2006.01)
*A61N 1/32* (2006.01)

(52) U.S. Cl.
CPC ..... *A61N 1/36014* (2013.01); *A61M 2205/05* (2013.01); *A61N 1/0452* (2013.01); *A61N 1/0484* (2013.01); *A61N 1/321* (2013.01)

(58) Field of Classification Search
USPC ............ 607/2, 3, 48, 62, 144; 600/386, 388; 604/28–30
See application file for complete search history.

(56) References Cited

U.S. PATENT DOCUMENTS

| | | | | |
|---|---|---|---|---|
| 4,715,849 | A * | 12/1987 | Gion | A61B 17/12 604/540 |
| 4,790,319 | A | 12/1988 | Slovak | |
| 4,883,462 | A | 11/1989 | Williamson et al. | |
| 4,942,880 | A | 7/1990 | Slovak | |
| 5,399,147 | A | 3/1995 | Kaiser | |
| 5,584,863 | A * | 12/1996 | Rauch | A61N 1/40 607/2 |
| 5,588,955 | A * | 12/1996 | Johnson et al. | 601/152 |
| 5,674,262 | A | 10/1997 | Tumey | |
| 5,957,860 | A | 9/1999 | Rodiera Olive | |
| 6,077,443 | A * | 6/2000 | Goldau | A61M 1/16 210/143 |
| 6,290,669 | B1 | 6/2001 | Zicherman | |
| 6,615,077 | B1 | 9/2003 | Zhu et al. | |
| 8,231,558 | B2 | 7/2012 | Singh | |
| 2002/0165590 | A1 | 11/2002 | Crowe et al. | |
| 2004/0023759 | A1* | 2/2004 | Duncan | A61N 1/36003 482/57 |
| 2005/0126578 | A1* | 6/2005 | Garrison | A61H 9/0078 128/874 |
| 2007/0142783 | A1* | 6/2007 | Huey | A61L 15/18 604/174 |
| 2011/0022103 | A1 | 1/2011 | Schrors | |

FOREIGN PATENT DOCUMENTS

| | | |
|---|---|---|
| WO | WO-2007014423 A1 | 2/2007 |
| WO | WO-2008155077 A1 | 12/2008 |

OTHER PUBLICATIONS

International Search Report and Written Opinion dated Feb. 16, 2009 in International Application No. PCT/IB2008/053375.

Queen's University (May 15, 2006). "Exercise During Dialysis Enhances Results and Overall Physical Performance." Science Daily. Retrieved Feb. 5, 2013, from http://www.sciencedaily.com-/releases/2006/05/060515100138.htm.

* cited by examiner

DEVICE FOR DIALYSIS AND STIMULATION OF A PATIENT AND METHOD

FIELD OF THE INVENTION

The present invention concerns devices for dialysis and stimulation of a patient, for example by electric muscle stimulation, by continuous passive motion (CPM) or by other physical stimulation means, and methods using this principle.

BACKGROUND OF THE INVENTION

Dialysis is a well known procedure of renal replacement therapy which is used to provide an artificial replacement for lost kidney function due to renal failure. Typically, in hemodialysis, a patient's blood is pumped through the blood compartment of a dialyzer, exposing it to a semipermeable membrane. Dialysis solution is pumped through the dialysate compartment of the dialyzer, which is configured so that the blood and dialysis solutions flow on opposite sides of the semipermeable membrane. The cleansed blood is then returned via the circuit back to the body of the patient.

It is also known in the art that physical exercise during dialysis improves the efficiency of dialysis.

For example, a news published in Science Daily on May 15, 2006 entitled "Exercise During Dialysis Enhances Results And Overall Physical Performance" discloses a study relating to this topic.

This news may be found on the internet at the following address.: http://www.sciencedaily.com/releases/2006/05/060515100138.htm According to this news which is based on a news release of the Queen's University (Kingston, Ontario, Canada), "a study suggests that patients who exercise while hooked up to dialysis show better results in clearing toxins and increasing overall physical stamina".

More specifically, according to the news "the study has shown that exercise during the process of dialysis increases by 20 percent the removal of urea, one of the toxins collected in the body between dialysis sessions. This indicates that exercise during dialysis can enhance the treatment".

Another article published by the Journal of the American Physical Therapy Association entitled "EFFECT OF EXERCISE DURING DIALYSIS ON QUALITY-OF-LIFE FOR INDIVIDUALS WITH END-STAGE RENAL DISEASE" by Ann M. Wilson; Nader Jabbour; Jamie Wilde*; Ryan Yorimoto; Kathleen Hummel-Berry Physical Therapy, University of Puget Sound, Tacoma, Wash., related to the same topic.

This article may be found on the internet at the following address. http://www.apta.org/am/abstracts/pt2005/abstractsPt.cfm?pubNo=PO-RR-38-TH According to this article "CONCLUSIONS: The preliminary results of this study support the premise that exercise can improve some aspects of health-related quality of life in individuals with ESRD [end-stage renal disease]. Further studies are needed to determine the long-term benefits of exercise during dialysis on quality-of-life".

Experimentally, an increase of 30% of dialysis treatment efficiency has been shown for a patient carrying out a physical exercise during dialysis (in this case a stationary bike).

However, average dialysis patient age is around 70 y (and many are handicapped) thus it is difficult or impossible to have them exercise properly.

Therefore, there is need for simple means and methods that would improve the dialysis and that may be used also by aged patients or patients with a limited mobility.

BRIEF DESCRIPTION OF THE INVENTION

The aim of the present invention is to improve the known devices and methods.

To this effect, the present invention proposes a device allowing dialysis and simulation of the patient (i.e. physical stimulation) at the same time, for example with an electrical stimulation and/or by continuous passive motion (CPM) and/or by other equivalent means that stimulate the body of the patient. More specifically, an idea is thus to Combine a physical stimulation (i.e. electric stimulation, CPM or other) with dialysis to improve efficacy of the procedure, allowing a better removal of Phosphate and urea as well as other toxins.

In the frame of the present invention, the notion of dialysis should be understood as meaning hemodialysis or peritoneal dialysis.

In one embodiment, the device of the present invention comprises a single body combining a dialysis apparatus and electrical stimulation apparatus.

In an other embodiment, the device comprises the combination of a dialysis machine and an electrical muscle stimulator machine.

In a further embodiment, the device comprises the combination of a dialysis machine and a continuous passive motion (CPM) system.

In another embodiment, the device comprises the combination of a dialysis machine with an inflatable/deflatable cuff.

In another embodiment of the invention, the device comprises a combination of a dialysis machine with several different stimulation devices (in particular the stimulation devices disclosed above).

In another embodiment, the device comprises a monitoring and controlling unit for monitoring and controlling the process.

As can be understood from the above description, an idea of the present invention is to combine a dialysis machine with an active stimulation device allowing the patient to remain passive during treatment.

An advantage of the device of the present invention is that it allows an increase in the blood pressure thus avoiding the risk of hypotension episodes during dialysis sessions.

The invention will be better understood from the description of embodiments with reference to the figures showing the principle.

DETAILED DESCRIPTION OF THE INVENTION

In the first embodiment, a dialysis machine 1, for example a hemodialysis machine, known per se in the art, is combined with an electric muscle stimulator 2. The electric muscle stimulator 2 comprises active zones such as electrodes 3 connected to a stimulator 2 via wires 4 or other equivalent means (wireless etc). Preferably, the electric muscle stimulator 2 is a constant current generator with near zero net charge per pulse to avoid chemical skin burns. The system can be further improved by a blood pressure sensor to trigger the electrical stimulation in case of blood pressure drop for example.

Figure 1:
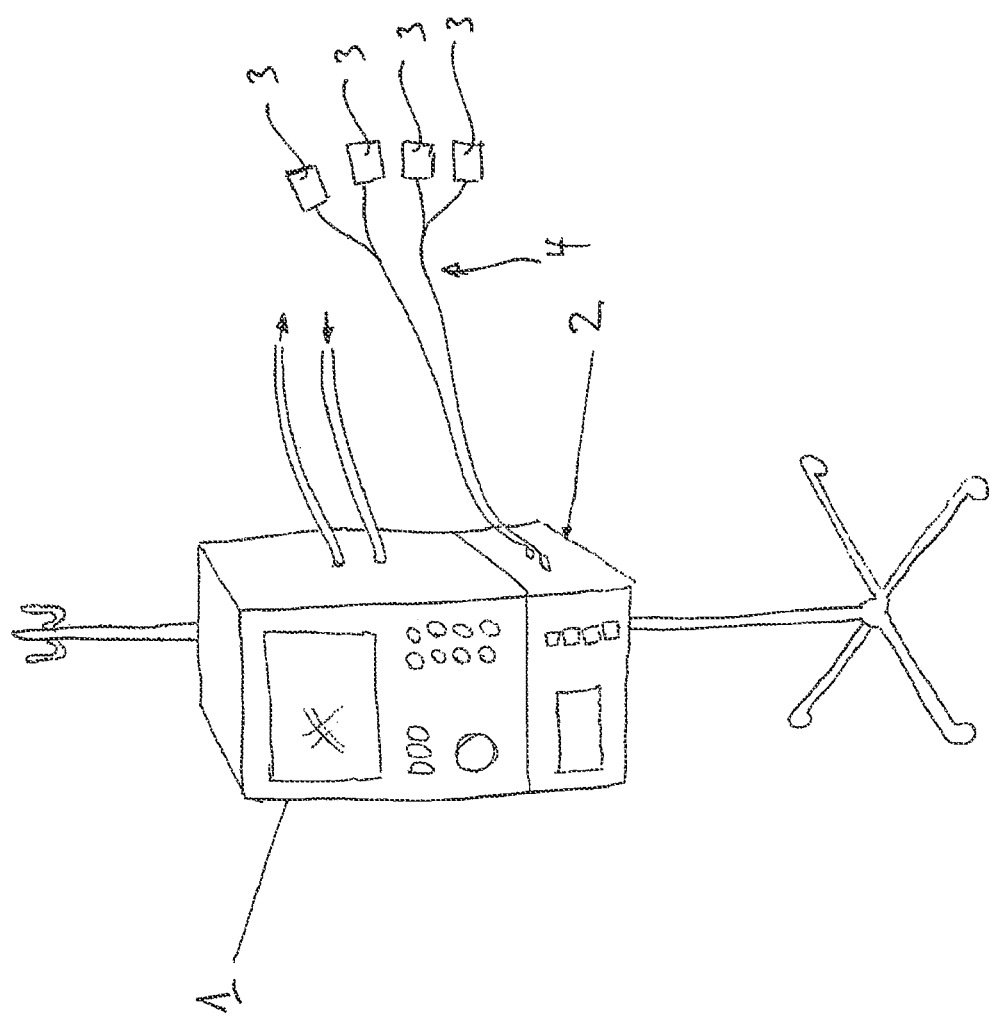
FIG. 1 illustrates in a schematical way a device according to the principle of the invention.

Of course, the device will include shielding means to avoid any interference between the stimulator and the dialysis machine. One way to solve this problem is to separate physically both devices but it is more handy and practical to have them together (as represented in an illustrative way in FIG. 1). The stimulator 2 could also be of a low emission type.

During a hemodialysis procedure, the patient muscles, preferably the legs muscles are stimulated electrically. Preferably, the means used will include a garment carrying the electrically active zone (electrodes) and/or an electrode with multiple electrical active zones, said garment or electrode being placed on the legs of the patient. Such garments are known in the art. Of course, it is also possible to place the electrode individually on the body of the patient.

During a peritoneal dialysis, the patient muscles, preferably the abdominal muscles are stimulated electrically. Preferably, the means used will include a garment (for example a belt) carrying the electrodes and/or an electrode with multiple electrical active zones, said garment or electrode being placed on the patient at a given place. Of course, it is also possible to place the electrode individually on the body of the patient. The use of a belt is advantageous in that it reinforces the abdominal muscles of the patient and avoids the risk of a hernia.

In a general way, when the stimulation frequency is less than about 20 Hz, the stimulation may be continuous.

If the frequency is between about 20 Hz and about 130 Hz, it is possible to combine contraction phases of stimulation with relaxation phases (with no stimulation at all or a stimulation at a frequency of less than 20 Hz).

It is also possible to use a TENS electrical stimulation for example in the range of 100 Hz to 150 Hz to avoid pain during treatment (for example when piercing the skin with a needle).

According to the invention, a low frequency is preferred for the electrical stimulation so that distinct muscle twitches are generated and not long tetanic contractions. Typically, the electrical stimulation of the muscle during dialysis has a frequency of about 2 to 8 Hz.

In another variant, the electrical stimulation of the muscles during dialysis, mainly of those of the legs, is made at a frequency of about 50 Hz. A sequential activation of the muscle from the extremities to the center of the body can also be used.

In another variant, electrical stimulation of the muscles with frequency of about 8 Hz can be administrated at patient's home between dialysis sessions to improve the overall treatment.

In a further variant, the electrical stimulation of the muscles is carried out at a frequency of about 10-20 Hz. This stimulation can also administrated at patient's home between dialysis sessions to improve the overall treatment.

In a further variant, the electrical stimulation of the muscles is carried out at a frequency of about 30 Hz. This stimulation can also administrated at patient's home between dialysis sessions to improve the overall treatment.

Furthermore, electrical stimulation can also be applied to the patient's arm of a newly arterio-venous fistula to accelerate the fistula maturation and/or for the treatment of postoperative pain Of course, electrical stimulation programs for increasing dialysis efficiency can be build by combining the preceding stimulation patterns to be used during dialysis sessions or also between such sessions.

Figure 2:
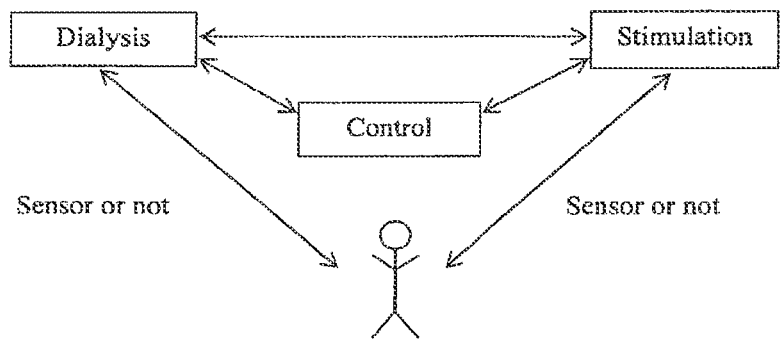
FIG. 2 illustrate a system and method based on the device of the invention.

FIG. 2 illustrates in a more general manner the principle of the invention. As will be described in the following, the present invention is not limited to an electrical stimulation but other types of stimulation can be applied to the patient during dialysis. Hence, the concept "stimulation" mentioned in FIG. 2 should be considered as covering other stimulations of the patient, as will be described in the following.

Accordingly, in another embodiment, the device comprises a dialysis machine, similar to the one described above, combined with a continuous passive motion (CPM) device for a physical stimulation of the patient.

As indicated above, it is possible to combine the electrical stimulation with other stimulation of the muscles, for example CPM. Such CPM systems are known per se in the art: CPM is a treatment method designed to aid in the recovery of joints after surgery. CPM is carried out by a CPM device, which constantly moves the joint through a small range of motion, the exact range is dependent upon the joint, but in most cases the range of motion is increased over time.

CPM is used as a rehab after surgery of various types of joint surgery such as knee replacement and ACL (anterior cruciate ligament) reconstructions.

When using CPM, it is preferred to use cycling motions but of course other motions (for example linear motions) may be envisaged. When cycling, typical rpm values are from about 0 to about 60 rpm.

In another embodiment, the stimulation device is an inflatable cuff, for example similar to the one known under the trade name "VenaFlow®" of Aircast®. Such cuffs usually have different shapes to suit individual physician preferences: calf, foot, and thigh. Each cuff is made from light, cool, comfortable material to promote increased patient compliance. Typically, the cuffs are latex-free and may be placed directly against the skin. With a slight adjustment, the patient may even move while wearing a cuff.

Systems as the "Aircast VenaFlow System" functions as a prophylaxis for deep vein thrombosis by using an effective combination of graduated sequential compression and rapid impulse inflation. This collaboration of technology assists in the prevention of thrombus formation.

More specifically, a "VenaFlow System" includes a pump with tube assembly and an inflatable/deflatable cuff, the pump being designed to operate with any of the cuffs. The pump's pressure and inflate/deflate cycle are preset and automatic or can be adjusted, with pressures shown on a display.

Of course, this is only an illustrative example and other equivalent cuffs or equivalent systems are possible in the scope of the present invention.

Figure 3:
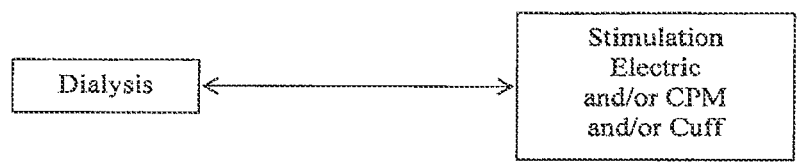
FIG. 3 illustrates a general representation of the method according to the present invention.

As will be readily understood from the above, the different stimulation techniques may be combined together, during dialysis sessions or between dialysis sessions as illustrated in FIG. 3.

One particular advantageous combination is the use of an inflatable cuff with electrodes to carry out a stimulation as in the VenaFlow® system with an electrical stimulation of muscles. The cuff is inflatable and can have the shape of a garment carrying electrically active zones. In the deflated configuration, it is usually easy to be put on a member of the patient (for example the leg) and once it is inflated the electrically active zones are properly in contact with the skin of the patient and an electric stimulation can be carried out. A further advantage is that the electrically active zones can be placed in fixed places and need not to be individually attached to the patient. Of course, it is possible to design other configurations in which the cuff/garment has openings (such as windows) in which the electrodes may be removably and individually applicable to the patient.

The electrical stimulation is applied preferably to the legs of the patient. Of course it is possible to stimulate other parts of the body of the patient, alone or in combination with the leg stimulation. As indicated above, the other stimulations can be applied to different patient's body parts.

The method according to the invention, in the first embodiment comprises at least the following steps:
applying dialysis to a patient;
during dialysis, applying an electrical stimulation to muscles of the patient.

In another embodiment, the method comprises the following steps:
applying dialysis to a patient;
during dialysis, applying a stimulation to the patient via a CPM device.

In another embodiment, the method comprises the following steps:
applying dialysis to a patient;
during dialysis, applying a stimulation to the patient via an inflatable/deflatable cuff.

In further embodiments of the method, the stimulation is carried out also in between dialysis sessions or only in between dialysis sessions. Such stimulations can be carried out via electrical stimulation means, CPM or an inflatable/deflatable cuff using the same or different programs as used during dialysis as indicated above or any suitable combination of stimulations.

In a further embodiment of the invention (as illustrated in FIG. 2), it is possible to envisage that the dialysis device and the stimulation device are linked together (for example via a wire or wireless) to monitor and control one another. To this effect, appropriate control and monitoring means may be used (illustrated by the block "Control" in FIG. 2).

For example, the dialysis device may control the stimulation device to carry out certain predetermined stimulation programs (for example as disclosed above) in a certain order or in a certain frequency or even with a certain intensity. One may also envisage that the control of the stimulation is made by measured parameters on the patient and adapted accordingly. Typical parameters include blood pressure, blood flow, elimination rate of waste (urea for example), haematocrit value, cardiac rhythm, respiration, oxygen rate.

The stimulation device may thus also comprise sensors to monitor the stimulation process (accelerometer, EMG) and feed back values to the dialysis device or to the stimulation device for monitoring of the overall process.

If the system uses an electrical stimulation, electrical sensed parameters and values may also be used to control the system and the stimulation.

Of course, the example given are non-limiting illustrations of the systems and methods according to the invention and variants are possible, also with equivalent means. For example, the stimulation frequencies can be varied with respect to the one indicated above to obtain the sought results.

In addition, other equivalent means may be envisaged to stimulate the muscles and the patient.

In the invention, the stimulation device can be attached to the dialysis in a fixed or removable manner (as for example illustrated in FIG. 1) and as said above the communication between the devices may be made through wires or wireless means.

An embodiment of the present invention comprises the combination of removable stimulation means with the controlling and monitoring means mentioned above. The removable stimulating device can hence be taken away by the patient (for example at home) in order to carry out stimulation sessions between dialysis sessions. Through the controlling and monitoring means, the necessary programs can be defined by the doctor or physician before the patient leaves and then, when the patient comes back for a dialysis session, the controlling and monitoring means can control that the stimulation sessions have been effectively carried out, for example by the downloading of relevant data memorized in the removable means. This allows a compliance monitoring and can also help in adjusting the treatment parameters applied to the patient in further sessions, for example by taking account of the sessions already effectively carried out, and/or in view of the results of previous sessions. Per se, portable stimulation devices are known in the art and their programming can be adapted to take account of the embodiment described hereabove.

The same principle can be applied to other stimulation devices (CPM, cuff). The control element illustrated in FIG. 2 can thus be used as a control box that is connected to the chosen simulation device (via wires of wireless), containing the stimulation programs to be carried out by the patient and also the results of the programs effectively carried out by the patient. To this effect, programming means and memory means are used.

The invention claimed is:

1. A method of treating a patient comprising:
providing a dialysis device and a stimulation device, the stimulation device including an inflatable/deflatable cuff having at least one electrode positioned thereon, the dialysis device linked with the inflatable/deflatable cuff such that the dialysis device can control the inflatable/deflatable cuff and the at least one electrode during a dialysis session;
applying dialysis to the patient with the dialysis device during a dialysis session;
during the dialysis session, applying physical stimulation to the patient via the stimulation device with the inflatable/deflatable cuff, by inflating and/or deflating the inflatable/deflatable cuff;
measuring blood pressure of the patient during the dialysis session with a sensor; and
when the blood pressure of the patient drops during the dialysis session, providing, with the at least one electrode, electrical stimulation to the patient at a certain frequency in an electrical stimulation program to activate the patient's muscles to increase the blood pressure of the patient.

2. The method of claim 1, wherein the method further comprises applying continuous passive motion (CPM) stimulation to the patient during dialysis.

3. The method of claim 2, wherein the CPM stimulation is a cycling motion at a frequency of about 0 to about 60 rpm.

4. The method of claim 1, further comprising applying a stimulation to the patient between a first dialysis session and a second dialysis session.

5. The method of claim 4, wherein said stimulation applied between the first and second dialysis sessions comprises at least one of stimulation made by an inflatable/deflatable cuff or continuous passive motion (CPM) stimulation.

6. The method of claim 1, wherein at least two different types of stimulation are used during dialysis.

7. The method of claim 1, wherein the stimulation applied by the inflatable/deflatable cuff is a combination of graduated sequential compression and rapid impulse inflation.

8. A system for carrying out dialysis and stimulation of a patient at the same time, comprising:
 a dialysis device;
 a sensor configured to measure blood pressure of a patient; and
 a stimulating device linked together with the dialysis device such that the dialysis device controls a dialysis session and controls the stimulating device to physically and electrically stimulate the patient during the dialysis session, the stimulating device comprising
 an inflatable/deflatable cuff for providing physical stimulation by inflation and deflation of the inflatable/deflatable cuff, and
 at least one electrode positioned on the inflatable/deflatable cuff for providing electrical stimulation to the patient during the dialysis session when the blood pressure of the patient drops, the stimulating device configured to provide electrical stimulation to the patient through the at least one electrode, in an electrical stimulation program, to activate the muscles of the patient to increase the blood pressure of the patient.

9. The system of claim 8, wherein the stimulating device is configured to provide electrical stimulation configured to sequentially activate muscles.

10. The system of claim 9, wherein the stimulating device is configured to provide electrical stimulation configured to sequentially activate muscles from an extremity toward a center of the patient's body.

11. The system of claim 8, wherein the dialysis device controls the stimulating device to carry out stimulation during dialysis based on one or more measured parameters on the patient selected from the consisting of: blood flow, urea elimination rate, haematrocrit value, cardiac rhythm, respiration, and oxygen rate.

12. The system of claim 8, wherein the stimulating device is configured to provide electrical stimulation via the at least one electrode at a frequency less than about 20 Hz.

13. The system of claim 8, wherein the stimulating device is configured to provide a TENS stimulation via the at least one electrode with a frequency between about 100 Hz to about 150 Hz.

14. The system of claim 8, wherein the stimulating device is configured to provide electrical stimulation via the at least one electrode at a frequency between about 2 Hz to about 8 Hz for producing distinct muscle twitches.

15. The system of claim 8, wherein the stimulating device is configured to provide electrical stimulation via the at least one electrode at a frequency of about 50 Hz.

16. The system of claim 8, wherein the cuff is shaped to fit a body part.

17. The system of claim 16, wherein the body part is a calf, foot or thigh.

18. The system of claim 8, wherein the cuff has the shape of a garment.

19. The system of claim 8, further comprising a continuous passive motion (CPM) device.

20. The system of claim 8, wherein the stimulation applied by the inflatable/deflatable cuff is a combination of graduated sequential compression and rapid impulse inflation.

21. The system of claim 8, wherein the device further comprises a monitor and a controller for monitoring and controlling the overall process.

22. The system of claim 8, wherein the dialysis device and the stimulating device are removably attached to each other.

23. The system of claim 8, wherein the link is made via wires or a wireless connection.

* * * * *

UNITED STATES PATENT AND TRADEMARK OFFICE
CERTIFICATE OF CORRECTION

PATENT NO. : 9,999,560 B2  
APPLICATION NO. : 13/961478  
DATED : June 19, 2018  
INVENTOR(S) : Stefan Farese Page 1 of 1

It is certified that error appears in the above-identified patent and that said Letters Patent is hereby corrected as shown below:

On the Title Page

Column 1, Item (*) Notice, Line 3, change "0 days. days." to --0 days.--

In the Specification

In Column 1, Line 3, below "METHOD", insert --This application is a continuation of United States Patent Application No. 12/674,599, currently pending, which is a national phase filing under 35 U.S.C. § 371 of International Application PCT/IB2008/053375, filed on August 22, 2008, which claims the benefit of European Patent Application No. 07114801.9 filed August 22, 2007 and European Patent Application No. 07119934.3 filed November 2, 2007, the contents of all of which are incorporated herein by reference in their entirety. International Application No. PCT/IB2008/053375 was published under PCT Article 21(2) in English.--

In Column 1, Line 32, change "address.:" to --address:--

In Column 1, Line 41, change "percent" to --per cent--

In Column 2, Line 14, change "Combine" to --combine--

Signed and Sealed this  
Twenty-second Day of January, 2019

Andrei Iancu  
*Director of the United States Patent and Trademark Office*